USO05562697A

United States Patent [19]
Christiansen

[11] Patent Number: 5,562,697
[45] Date of Patent: Oct. 8, 1996

[54] SELF-EXPANDING STENT ASSEMBLY AND METHODS FOR THE MANUFACTURE THEREOF

[75] Inventor: Frank K. Christiansen, Haslev, Denmark

[73] Assignee: William Cook, Europe A/S, Denmark

[21] Appl. No.: 529,474

[22] Filed: Sep. 18, 1995

[51] Int. Cl.$^6$ .......................... A61M 29/00; A61F 2/06; A61F 2/04

[52] U.S. Cl. .......................... 606/191; 606/195; 606/198; 623/1; 623/12

[58] Field of Search ...................... 606/191, 195, 606/198; 623/1, 12

[56] References Cited

U.S. PATENT DOCUMENTS

| 4,580,568 | 4/1986 | Gianturco | 606/195 |
|---|---|---|---|
| 4,813,934 | 3/1989 | Engelson et al. | 606/195 |

FOREIGN PATENT DOCUMENTS

| 0480667 | 4/1992 | European Pat. Off. . |
| 9206734 | 4/1992 | WIPO . |

Primary Examiner—Michael Powell Buiz
Assistant Examiner—Kevin Truong
Attorney, Agent, or Firm—Richard J. Godlewski

[57] ABSTRACT

A self-expanding stent assembly and methods for the manufacture thereof and for introduction of such a stent assembly into a body passage or duct of a patient. A self-expanding endovascular stent assembly comprises at least one stent segment (7, 8) formed by a single piece of wire arranged in a closed zig-zag configuration with struts (10) joining each other joints (11) and a covering sleeve (9). The stent segment (7, 8) is compressible from an expanded condition with a first radius (R) into an introduction condition with second radius (r). The struts (10) are retained solely by the sleeve (9), which is relatively inelastic and has a thickness of not more than 1 percent of the first radius (R).

14 Claims, 2 Drawing Sheets 5,562,697

SELF-EXPANDING STENT ASSEMBLY AND METHODS FOR THE MANUFACTURE THEREOF

TECHNICAL FIELD

This invention relates generally to medical devices and, in particular, to a self-expanding stent assembly.

BACKGROUND OF THE INVENTION

Endovascular stents are generally used in preventing restenosis or closure by tumors of passageways and ducts in the body of a patient and for percutaneous repair of aneurysms.

From EP-A-0 480 667, a stent assembly of this kind is known in which the metal wire bodies of one or more stent segments are surrounded by a flexible, elastic sleeve, e.g. of nylon, covering the gaps between the struts of the metal wire bodies. The joints between the struts at either end of each segment are shaped into eyes by bending the wire to form a cusp and, then, welding or soldering the wire back upon itself. The stent segments are firmly attached to the flexible sleeve either by stitching, gluing or embedding the segments in the sleeve when the latter is made of a plastic material. The stent segments are connected with each other by tying the eyes formed at the joints of two segments with thread.

Whereas this prior art device is capable of percutaneous implantation, e.g. in the biliary duct, and is effective for permanent prevention of ingrowth of a tumor between the struts of the segment due to the flexible sleeve, it suffers from various practical disadvantages. On one hand, the manufacture is relatively complicated due to the welding or soldering operation required for forming the eyes at the joints of the struts and the mutual connection of stent segments by tying the eyes of two stent segments positioned end to end with thread. Since proper implantation requires the stent assembly to be able to resist contraction along the axis, application of the sleeve material to the stent segments must take place in the compressed condition of the latter.

Moreover, the thread used for tying the eyes of two segments together will add to the minimum thickness of the stent in the compressed condition which sets a lower limit to the internal diameter of the catheter used for percutaneous introduction.

From published international patent application WO 92/06734, a multistage stent assembly is known which is made up of a number of unit structures that are prevented from separation by means of rod-like connecting members joining the bends of appointed structures together. The assembly is wrapped by a mesh made, e.g., of nylon coated with silicone rubber. Also in this prior art stent, the additional connecting members will add to the minimum thickness of the stent assembly in the collapsed condition.

SUMMARY OF THE INVENTION

It is the object of the invention to provide an improved endovascular stent assembly of the kind defined above offering the advantages of a less complicated manufacture and a further reduced overall diameter in the collapsed condition used for introduction of the stent, thereby permitting introduction through a relatively narrow catheter as well as an improved flexibility without any tendency to kinking in the collapsed condition so as to permit easy introduction also through curved or narrow passageways or ducts.

According to the invention, a self-expanding stent assembly of the kind defined is characterized in that the struts of said metal wire body are retained solely by said sleeve, said sleeve being relatively inelastic and having a thickness of not more than 1 percent of said first radius.

By retaining the struts of the metal wire body of each stent segment solely by the relatively inelastic, but still flexible sleeve of a small thickness the connecting threads or rods used in the above-mentioned prior art structures are avoided, so that in addition to the thin sleeve itself the only elements to be elastically deformed in the collapsed condition will be the wire struts. The use of a relatively inelastic sleeve permits application of the sleeve material to the stent segment or segments in their expanded uncompressed condition.

As a result thereof in a multistage embodiment of the stent assembly of the invention, several coaxial stent segments will be connected solely through the sleeve and be axially displaced relative to one another to permit axial expansion of each stent segment in the compressed condition.

The invention also relates to a method of manufacturing a self-expanding stent assembly of the kind set forth, which is characterized in that at least one stent segment is made by forming a metal wire body from a single piece of wire arranged in a closed zig-zag configuration with a series of struts and joints to form a mainly cylindrical shape having said first radius, a plastic film covering being applied to said metal wire body in a thickness not exceeding 1 percent of said first radius in such a way as to connect said film material with the wire material of said metal wire body in said joints.

Moreover, the invention also relates to a method of intruding the self-expanding stent assembly into a passageway or duct of a patient, which is characterized by the use of an introduction catheter having an internal radius not exceeding 25 percent of said first radius.

BRIEF DESCRIPTION OF THE DRAWING

In the following the invention will be further explained with reference to the accompanying schematical drawings, in which.

DETAILED DESCRIPTION

The invention relates to a self-expanding endovascular stent assembly comprising at least one stent segment with a metal wire body formed by a single piece of wire arranged in a closed zig-zag configuration including an endless series of struts joining each other in an equal number of joints and a covering sleeve made of a bio-compatible plastic film material, said stent segment being compressible from an expanded condition of a mainly cylindrical shape having a first radius into an introduction condition in which it assumes a smaller second radius.

Figure 1:
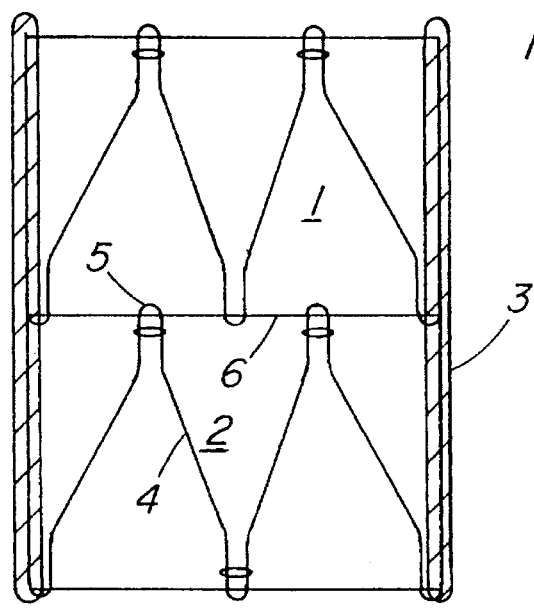
FIG. 1 depicts a partial side representation of a prior art stent assembly as disclosed in EP-A-0 480 667 mentioned above.

FIG. 1 depicts two segments 1 and 2 of the prior art stent known from EP-A-0 480 667 surrounded by a flexible elastic sleeve 3 which may be of nylon and to which segments 1 and 2 are firmly attached by stitching, gluing or being embedded in sleeve 3. Each of segments 1 and 2 is formed from a metal wire body formed from a single piece of wire arranged in a closed zig-zag configuration with an endless series of struts 4 joining each other in joints 5 shaped into eyes which are tied with thread 6 to connect segments 1 and 2 with each other.

Figure 2:
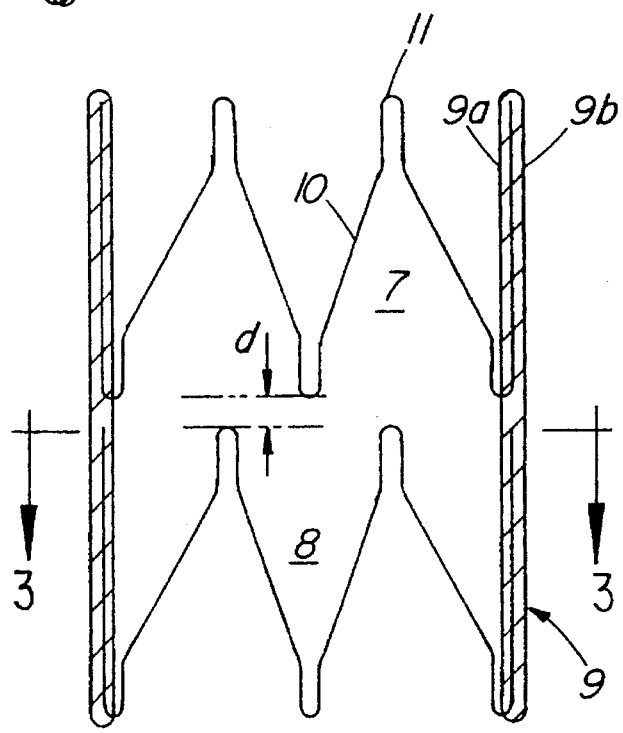
FIG. 2 depicts a partial side representation of an embodiment of the stent assembly according to the invention in its expanded condition.

In FIG. 2, two segments 7 and 8 of an embodiment of a stent assembly according to the invention is depicted in the expanded state assumed in the position of use of the stent. segments 7 and 8 are in this embodiment connected solely through the surrounding sleeve 9, i.e., without tying the joints 11 between the struts 10 together. The sleeve 9 is made of a relatively inelastic material such as high density polyethylene and has a small thickness of not more than 1 percent of the radius R of the stent in the expanded condition as also depicted in FIG. 3, said thickness being preferably not greater than 30μ, but preferably at least 20μ.

Figure 3:
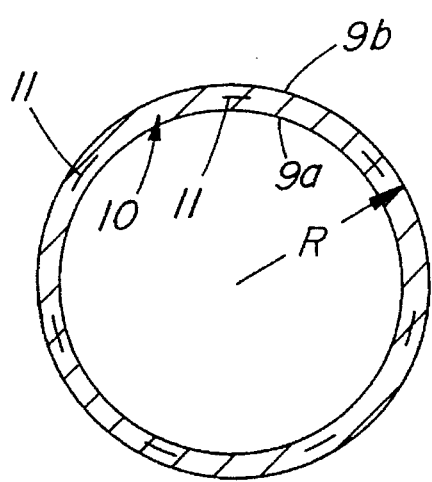
FIG. 3 depicts a cross-sectional representation of the stent assembly in FIG. 2.

As depicted in FIG. 3, sleeve 9 may, in order to retain the metal wire bodies of segments 7 and 8, be composed of two layers of film 9a and 9b each having a thickness of, e.g., 12μ.

Figure 4:
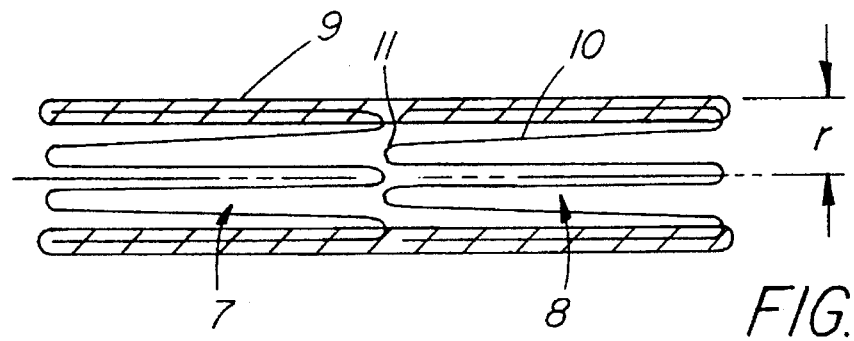
FIG. 4 depicts a side representation of the stent assembly in FIGS. 2 and 3 in a partly compressed condition.

In FIG. 4, the stent assembly of FIGS. 2 and 3 is depicted in its compressed state of introduction in which the radius r is substantially smaller than radius R in the expanded state.

Figure 5:
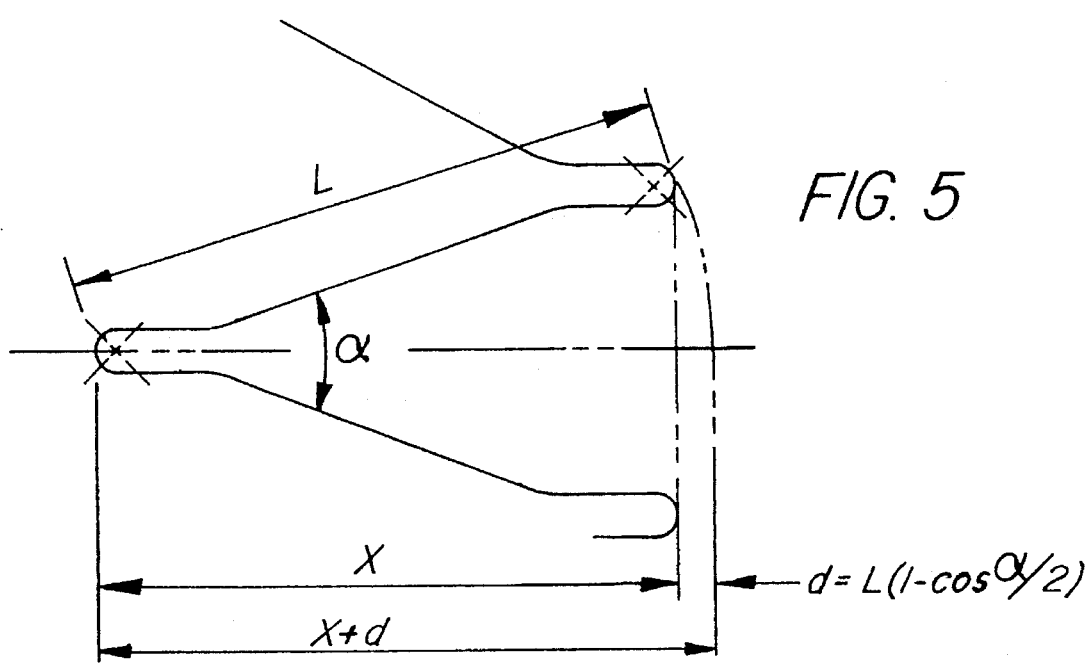
FIGS. 5 and 6 depict schematical illustrations of the dimensional features of the stent assembly according to the invention.
Figure 6:
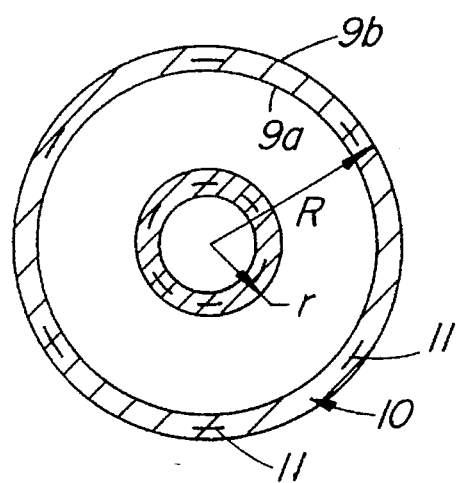

Since, for the stent assembly of the invention, the sleeve 9 is applied to stent segments 7 and 8 in the expanded state due to the relative inelastic properties of the sleeve material, segments 7 and 8 are arranged in sleeve 9 to be axially displaceable with a mutual separation d in the expanded state which is more clearly apparent from FIGS. 2 and 5 and is determined by $$d=L(1-\cos \alpha/2),$$

where L is the length of each of the struts 10, and $\alpha$ is the angle included between two successive struts 10 of the metal wire body of each segment 7 or 8. As also depicted in FIG. 5, x represents the axial length of each segment 7 or 8 in the expanded state, and x+d represents the axial length of each segment 7 or 8 in the compressed state of introduction.

Thereby, compression of the stent into the introduction state shown in FIG. 4 without segments 7 and 8 conflicting with or overlapping each other is made possible.

Since segments 7 and 8 are firmly attached to sleeve 9 and are not tied together by an additional thread as in the prior art stent of FIG. 1, the external radius r in the introduction state may be minimized.

Thus, assuming that the metal wire body of each of segments 7 and 8 is made up of 13 struts joining each other in 7 joints and further that the wire thickness of each strut is 0.25 mm, the radius of curvature of each joint is 0.32 mm and the sleeve 9 is composed of two layers of film each with a thickness of 12μ the area of occupation of the sleeve 9 would for an external radius R=5 mm in the expanded state amount to $$A_{sleeve}=2\pi(5^2-4.9888^2)=0.753 \text{ mm}^2$$

and the area of occupation of the metal wire body in the compressed state would ideally amount to $$A_{sleeve}=2(0.32+0.25)\times 0.25 \times 7=1.995 \text{ mm}^2$$

Thereby, the total area of occupation would be $$A_{sleeve}+A_{metal}=2.748 \text{ mm}^2$$

and the stent would easily fit into a 7 French introducer sheath of a diameter of 2.33 mm and an internal cross sectional area of 4.276 mm².

What is claimed is:

1. A self-expanding endovascular stent assembly comprising at least one stent segment (7, 8) with a metal wire body formed by a single piece of wire arranged in a closed zigzag configuration including an endless series of struts (10) joining each other in an equal number of joints (11) and a covering sleeve (9) made of a bio-compatible plastic film material, said stent segment (7, 8) being compressible from an expanded condition of a mainly cylindrical shape having a first radius (R) into an introduction condition in which it assumes a smaller second radius (r), wherein the struts (10) of said metal wire body are retained solely by said sleeve (9), said sleeve being relatively inelastic and having a thickness of not more than 1 percent of said first radius (R).

2. A self-expanding stent assembly as claimed in claim 1 further comprising several stent segments (7, 8) which are axially displaceable with a mutual separation and are connected solely through said sleeve (9).

3. A self-expanding stent assembly as claimed in claim 2 wherein said mutual separation is greater than L(1−cos α/2), where L is the length of each of said stent segments (7, 8) and α is the angle included between two successive struts (10) of said metal wire body.

4. A self-expanding stent assembly as claimed in claim 1 wherein said sleeve (9) is made of high density polyethylene.

5. A self-expanding stent assembly as claimed in claim 2 wherein said sleeve (9) is made of high density polyethylene.

6. A self-expanding stent assembly as claimed in claim 3 wherein said sleeve (9) is made of high density polyethylene.

7. A self-expanding stent assembly as claimed in claim 4 wherein said second radius (r) is smaller than 25 percent of said first radius (R).

8. A self-expanding stent assembly as claimed in claim 7 wherein at a value of said first radius (R) of 5 mm, the thickness of said sleeve (9) is not greater than 30μ.

9. A self-expanding stent assembly as claimed in claim 8 wherein the thickness of said sleeve (9) is at least 20μ.

10. A self-expanding stent assembly as claimed in claim 9 wherein said joints (11) have a radius of curvature not exceeding 1.3 times the wire thickness.

11. A self-expanding stent assembly as claimed in claim 10 wherein said metal wire body comprises 7 joints (11).

12. A method of manufacturing a self-expanding stent assembly comprising the steps of: making at least one stent segment (7, 8) with a metal wire body formed from a single piece of wire arranged in a closed zig-zag configuration with a series of struts (10) and joints (11), forming a mainly cylindrical shape having a first radius (R) and applying a plastic film to said metal wire body in a thickness not exceeding 1 percent of said first radius (R) in such as way as to connect said film with the wire of said metal wire body in said joints (11).

13. A method of introducing a self-expanding stent assembly into a body passage of a patient, said self-expanding stent assembly comprising at least one stent segment (7, 8) with a metal wire body formed by a single piece of wire arranged in a closed zig-zag configuration including an endless series of struts (10) joining each other in an equal number of joints (11) and a covering sleeve (9) made of a bio-compatible plastic film material, said stent segment (7, 8) being compressible from an expanded condition of a mainly cylindrical shape having a first radius (R) into an introduction condition in which it assumes a smaller second radius (r), wherein the struts (10) of said metal wire body are retained solely by said sleeve (9), said sleeve being relatively inelastic and having a thickness of not more than 1 percent of said first radius (R), said method comprising the steps of providing an introduction catheter having an internal radius not exceeding 25 percent of said first radius (R) and introducing said self-expanding stent assembly into a body passage of a patient with said catheter.

14. A method as claimed in claim 13 wherein at a value of said first radius of 5 mm said introduction is conducted through a catheter having an internal diameter of 7 French (2.33 mm).

* * * * *